(12) United States Patent
Meskens et al.

(10) Patent No.: US 9,161,140 B2
(45) Date of Patent: Oct. 13, 2015

(54) MEDICAL DEVICE FOR LESSENING THE EFFECTS OF NOISE AND INTERFERENCE FROM VARYING OR ALTERNATING MAGNETIC FIELDS

(71) Applicants: Werner Meskens, Mechelen (BE); Guilhem Vavelin, Sidney (AU)

(72) Inventors: Werner Meskens, Mechelen (BE); Guilhem Vavelin, Sidney (AU)

(73) Assignee: Cochlear Limited, Macquarie University (AU)

( * ) Notice: Subject to any disclaimer, the term of this patent is extended or adjusted under 35 U.S.C. 154(b) by 57 days.

(21) Appl. No.: 14/166,571

(22) Filed: Jan. 28, 2014

(65) Prior Publication Data
US 2015/0215708 A1    Jul. 30, 2015

(51) Int. Cl.
*A61N 1/375* (2006.01)
*H04R 25/00* (2006.01)
*H04R 9/02* (2006.01)
*H04R 3/08* (2006.01)
*A61N 1/08* (2006.01)

(52) U.S. Cl.
CPC ............... *H04R 25/554* (2013.01); *A61N 1/08* (2013.01); *A61N 1/3758* (2013.01); *H04R 3/08* (2013.01); *H04R 9/025* (2013.01); *H04R 25/558* (2013.01); *H04R 25/606* (2013.01); *H04R 2225/49* (2013.01)

(58) Field of Classification Search
None
See application file for complete search history.

(56) References Cited

U.S. PATENT DOCUMENTS

| | | | |
|---|---|---|---|
| 6,067,474 A | 5/2000 | Schulman et al. | |
| 7,289,853 B1 * | 10/2007 | Campbell et al. | 607/32 |
| 8,280,524 B2 * | 10/2012 | Duftner et al. | 607/65 |
| 8,515,112 B2 | 8/2013 | Crawford et al. | |
| 2011/0224789 A1 | 9/2011 | Griffith | |
| 2012/0197345 A1 | 8/2012 | Staller | |

\* cited by examiner

*Primary Examiner* — Kennedy Schaetzle
(74) *Attorney, Agent, or Firm* — McDonnell Boehnen Hulbert & Berghoff LLP (57) ABSTRACT

An external device of an implantable medical system includes a coil that is substantially disposed in an XY-plane. When a first AC electrical signal is passed through the coil, the coil generates an alternating magnetic field that represents the AC electrical signal. The electrical signal can include at least one of power or data. The device also includes a cylindrical shaped permanent magnet with base substantially parallel to the XY-plane. The magnet can be is used to position the external device with respect to an implantable device. Further, the device has a printed circuit board that includes at least a portion that is substantially orthogonal to the XY-plane and the portion can also include an electrical ground plane. In addition, the device can include at least one sensor that is coupled to the portion of the substrate and to the ground plane.

20 Claims, 8 Drawing Sheets

MEDICAL DEVICE FOR LESSENING THE EFFECTS OF NOISE AND INTERFERENCE FROM VARYING OR ALTERNATING MAGNETIC FIELDS

BACKGROUND

An electronic device can be affected by noise and interference from a variety of sources. One source of noise and interference is a varying or alternating magnetic field that can induce undesirable eddy currents in the electronic device. In one example, a varying magnetic field is used to communicate data signals and/or power over an electromagnetic radio frequency (RF) link between electronic devices or components. In this example, the varying magnetic fields can induce eddy currents that adversely affect signal quality and power efficiency of the RF link.

Some hearing prostheses include separate electronic components that are configured to communicate with each other over an electromagnetic RF link. In this example, the RF link allows data communication and/or power transfer between the components. In one example, a hearing prosthesis includes a first component that is external to the person and a second component that is at least partially implanted in the person. In this example, the first component detects sound, encodes the detected sound as acoustic signals, and transmits the acoustic signals to the second component over an electromagnetic RF link between the first and second components. More particularly, the first component generates a varying magnetic field that represents the acoustic signals. The second component receives the varying magnetic field and extracts the acoustic signals. Further, the second component applies the acoustic signals as output signals to the person's hearing system so that the person can perceive the output signals as sound. The output signals applied to the person's hearing system can include, for example, audible signals, vibrations, and/or electrical signals. As discussed generally above, the varying magnetic field generated by the first component can be a source of noise and interference in the first and second components. Generally, it is desirable to design electronic devices in order to reduce undesirable effects of noise and interference and to improve power efficiency.

SUMMARY

The present disclosure relates to the design of an electronic device to help lessen the effects of noise and interference from a varying or alternating magnetic field. Generally, the present disclosure configures electrical components of the device and electrical ground planes coupled to the components so that the components and ground planes are substantially parallel to the varying magnetic field. Such a configuration of the components and ground planes lessens the effects of noise and interference from the varying magnetic field by decreasing a magnetic flux of the magnetic field that passes through the components and electrical conductive parts.

In one aspect, the electronic device includes electrical components configured to generate the varying magnetic field. Further, the electronic device includes a substrate that is positioned substantially parallel to the varying magnetic field generated by the electrical components. One or more other electrical components can be coupled to the substrate. Further, the substrate can include an electrical ground plane that is coupled to the one or more other electrical components, such that the ground parallel is also positioned substantially parallel to the varying magnetic field.

The above and additional aspects, examples, and embodiments are further described in the present disclosure.

DETAILED DESCRIPTION

The following detailed description sets forth various features and functions of the disclosed embodiments with reference to the accompanying figures. In the figures, similar reference numbers typically identify similar components, unless context dictates otherwise. The illustrative embodiments described herein are not meant to be limiting. Aspects of the disclosed embodiments can be arranged and combined in a variety of different configurations, all of which are contemplated by the present disclosure. For illustration purposes, some features and functions are described with respect to medical devices, such as hearing prostheses. However, the features and functions disclosed herein may also be applicable to other types of devices, including other types of medical and non-medical devices.

Figure 1:
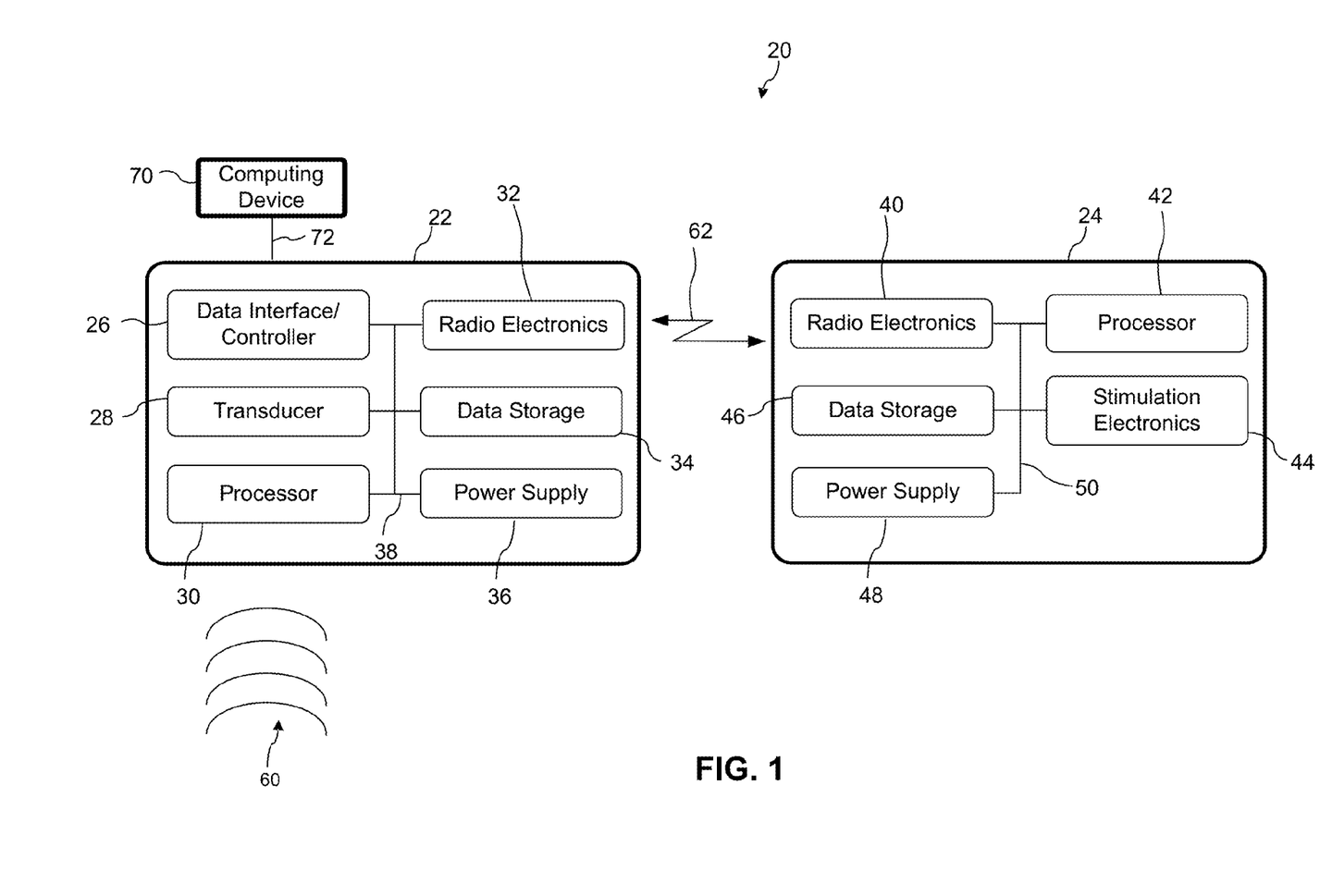
FIG. 1 is a block diagram of a hearing prosthesis according to an embodiment of the present disclosure.

Referring now to FIG. 1, an example electronic device 20 includes a first component or unit 22 and a second component or unit 24. The device 20 can be a hearing prosthesis, such as a cochlear implant, an acoustic hearing aid, a bone-anchored device, a direct acoustic cochlear stimulation device, an auditory brainstem implant, a bimodal hearing prosthesis, or any other type of hearing prosthesis configured to assist a prosthesis recipient to perceive sound. In this context, the first unit 22 can be generally external to a recipient and communicate with the second unit 24, which can be implanted in the recipient. In other examples, the units 22, 24 can both be at least partially implanted or can both be at least partially external to the recipient. In yet other examples, the first and second units 22, 24 may form separate components of a single operational device. Generally, an implantable unit or device can be hermetically sealed and otherwise adapted to be at least partially implanted in a person.

In FIG. 1, the first unit 22 includes a data interface or controller 26 (such as a universal serial bus (USB) controller), one or more transducers 28, one or more processors 30 (such as digital signal processors (DSPs)), radio electronics 32 (such as an electromagnetic radio frequency (RF) transceiver), data storage 34, and a power supply 36, all of which are illustrated as being coupled directly or indirectly via a wired conductor or wireless link 38. In the example of FIG. 1, the second device 24 includes radio electronics 40 (such as another RF transceiver), one or more processors 42, stimulation electronics 44, data storage 46, and a power supply 48, all of which are illustrated as being coupled directly or indirectly via a wired conductor or wireless link 50.

The transducer 28 can include a microphone that is configured to receive external acoustic signals 60. Further, the microphone can include combinations of one or more omnidirectional or directional microphones that are configured to receive background sounds and/or to focus on sounds from a specific direction, such as generally in front of the prosthesis recipient. Alternatively or in conjunction, the device 20 is configured to receive sound information from other sources, such as electronic sound information received through the data interface 26 of the first unit 22 or through the radio electronics 40 of the second device 24.

In one example, the processor 30 of the first unit 22 is configured to convert or encode the acoustic signals 60 (or other electronic sound information) into encoded acoustic signals that are applied to the radio electronics 32. In the present example, the radio electronics 32 of the first unit 22 are configured to transmit the encoded acoustic signals as output signals 62 to the radio electronics 40 of the second device 24. Illustratively, the radio electronics 32, 40 can include magnetically coupled coils that establish an RF link between the units 22, 24. Accordingly, the radio electronics 32 can transmit the output signals 62 encoded in a varying or alternating magnetic field over the RF link between the units 22, 24.

Generally, the radio electronics 32 can include an RF inductive transmitter system or circuit. Such a transmitter system may further include an RF modulator, a transmitting coil, and associated circuitry for driving the coil to radiate the output signals 62 as electromagnetic RF signals. Illustratively, the RF link can be an On-Off Keying (OOK) modulated 5 MHz RF link, although different forms of modulation and signal frequencies can be used in other examples.

As mentioned above, the processor 30 converts the acoustic signals 60 into encoded acoustic signals that are transmitted as the output signals 62 to the radio electronics 40. More particularly, the processor 30 utilizes configuration settings, auditory processing algorithms, and a communication protocol to convert the acoustic signals 60 into acoustic stimulation data that are encoded in the output signals 62. One or more of the configuration settings, auditory processing algorithms, and communication protocol information can be stored in the data storage 34. Illustratively, the auditory processing algorithms may utilize one or more of speech algorithms, filter components, or audio compression techniques. The output signals 62 can also be used to supply power to one or more components of the second unit 24.

The acoustic stimulation data can then be applied to the stimulation electronics 44 of the second unit 24 to allow a recipient to perceive the acoustic signals 60 as sound. Generally, the stimulation electronics 44 can include a transducer that provides auditory stimulation to the recipient through one or more of electrical nerve stimulation, audible sound production, or mechanical vibration of the cochlea, for example.

In the present example, the communication protocol defines how the stimulation data is transmitted from the first unit 22 to the second unit 24. For example, the communication protocol can be an RF protocol that is applied after the stimulation data is generated to define how the stimulation data will be encoded in a structured signal frame format of the output signals 62. In addition to the stimulation data, the communication protocol can define how power signals are supplied over the structured signal frame format to provide a more continuous power flow to the second unit 24 to charge the power supply 48, for example. Illustratively, the structured signal format can include output signal data frames for the stimulation data and additional output signal power frames. In one example, the output signal power frames include pseudo-data to fill in partially a death time associated with the signal, which facilitates the more continuous power flow to the second unit. However, in other examples, additional output signal power frames are not necessary to transmit sufficient power to the second unit, because there may be enough "one" data cells of the stimulation data to provide power and/or a carrier wave of the output signals 62 may provide sufficient power.

Once the stimulation data and/or power signals are encoded using the communication protocol, the encoded stimulation data and/or power signals can be provided to the radio electronics 32, which can include an RF modulator. The RF modulator can then modulate the encoded stimulation data and/or power signals with the carrier signal, e.g., a 5 MHz carrier signal, and the modulated 5 MHz carrier signal can then be transmitted over the RF link from the radio electronics 32 to the radio electronics 40. In various examples, the modulations can include OOK or frequency-shift keying (FSK) modulations based on RF frequencies between about 100 kHz and 50 MHz.

The second unit 24 receives the RF output signals 62 via the radio electronics 40. In one example, the radio electronics 40 include a receiving coil and associated circuitry for receiving electromagnetic RF signals, such as the output signals 62. The processor 42 is configured to decode the output signals 62 and extract stimulation data. The processor 42 can then apply the stimulation data to the recipient via the stimulation electronics 44. When the output signals 62 include power signals, the radio electronics 40 are configured to apply the received output signals 62 to charge the power supply 48.

As described above, the radio electronics 32 can be configured to transmit data and power to the radio electronics 40. In like manner, the radio electronics 40 can be configured to transmit signals to the radio electronics 32, and the radio electronics 32 can be configured to receive signals from the second unit 24 or other devices or units.

Referring back to the stimulation electronics 44, these electronics can take various forms depending on the type of hearing prosthesis. Illustratively, in embodiments where the hearing prosthesis 20 is a direct acoustic cochlear stimulation (DACS) device, the microphone 28 is configured to receive the acoustic signals 60, and the processor 30 is configured to encode the acoustic signals into the output signals 62. In this example, the radio electronics 40 receive the output signals 62, and the processor 42 applies the output signals to the DACS recipient's inner ear via the stimulation electronics 44. In the present example, the stimulation electronics 44 includes or is otherwise connected to an auditory nerve stimulator to transmit sound to the recipient via direct mechanical stimulation.

Similarly, for embodiments where the hearing prosthesis 20 is a bone anchored device, the microphone 28 and the processor 30 are configured to receive, analyze, and encode acoustic signals 60 into the output signals 62. The radio electronics 40 receive the output signals 62, and the processor 42 applies the output signals to the bone anchored device recipient's skull via the stimulation electronics 44 that includes or is otherwise connected to an auditory vibrator to transmit sound to the recipient via direct bone vibrations, for example.

In addition, for embodiments where the hearing prosthesis 20 is an auditory brain stem implant, the microphone 28 and the processor 30 are configured to receive, analyze, and encode the acoustic signals 60 into the output signals 62. The radio electronics 40 receive the output signals 62, and the processor 42 applies the output signals to the auditory brain stem implant recipient's auditory nerve via the stimulation electronics 44 that, in the present example, includes or is otherwise connected to one or more electrodes.

Similarly, in embodiments where the hearing prosthesis 20 is a cochlear implant, the microphone 28 and the processor 30 are configured to receive, analyze, and encode the external acoustic signals 60 into the output signals 62. The radio electronics 40 receive the output signals 62, and the processor 42 applies the output signals to an implant recipient's cochlea via the stimulation electronics 44. In this example, the stimulation electronics 44 includes or is otherwise connected to an array of electrodes.

In embodiments where the hearing prosthesis 20 is an acoustic hearing aid or a combination electric and acoustic hybrid hearing prosthesis, the microphone 28 and the processor 30 are configured to receive, analyze, and encode acoustic signals 60 into output signals 62. The radio electronics 40 receive the output signals 62, and the processor 42 applies the output signals to a recipient's ear via the stimulation electronics 44 comprising a speaker, for example.

Referring now to the power supplies 36, 48, each power supply provides power to various components of the first and second units 22, 24, respectively. The power supplies 36, 48 can be any suitable power supply, such as non-rechargeable or rechargeable batteries. In one example, one or more both of the power supplies 36, 48 are batteries that can be recharged wirelessly, such as through inductive charging. Generally, a wirelessly rechargeable battery facilitates complete subcutaneous implantation of a device to provide fully or at least partially implantable prostheses. A fully implanted hearing prosthesis has the added benefit of enabling the recipient to engage in activities that expose the recipient to water or high atmospheric moisture, such as swimming, showering, saunaing, etc., without the need to remove, disable or protect, such as with a water/moisture proof covering or shield, the hearing prosthesis. A fully implanted hearing prosthesis also spares the recipient of stigma, imagined or otherwise, associated with use of the prosthesis.

Referring to the data storage 34, 46, these components generally include any suitable volatile and/or non-volatile storage components. Further, the data storage 34, 46 may include computer-readable program instructions and perhaps additional data. In some embodiments, the data storage 34, 46 stores data and instructions used to perform at least part of the herein-described processes and/or at least part of the functionality of the systems described herein. Although the data storage 34, 46 in FIG. 1 are illustrated as separate blocks, in some embodiments, the data storage can be incorporated into other components of the units 22, 24, such as the processor(s) 30, 42, respectively.

The device 20 illustrated in FIG. 1 further includes a computing device 70 that is configured to be communicatively coupled to the first unit 22 (and/or the second unit 24) via a connection or link 72. The link 72 may be any suitable wired connection, such as an Ethernet cable, a Universal Serial Bus connection, a twisted pair wire, a coaxial cable, a fiber-optic link, or a similar physical connection, or any suitable wireless connection, such as Bluetooth, Wi-Fi, WiMAX, inductive or electromagnetic coupling or link, and the like.

In general, the computing device 70 and the link 72 are used to operate the device 20 in various modes. In a first example mode, the computing device 70 is used to develop and/or load a recipient's configuration data to the device 20, such as through the data interface 26. In another example mode, the computing device 70 is used to upload other program instructions and firmware upgrades, for example, to the device 20. In yet other example modes, the computing device 70 is used to deliver data (e.g., sound information) and/or power to the device 20 to operate the components thereof and/or to charge one or more of the power supplies 36, 48. Still further, various other modes of operation of the prosthesis 20 can be implemented by utilizing the computing device 70 and the link 72.

The computing device 70 can further include various additional components, such as a processor and a power source. Further, the computing device 70 can include a user interface or input/output devices, such as buttons, dials, a touch screen with a graphical user interface, and the like, that can be used to turn the one or more components of the device 20 on and off, adjust the volume, switch between one or more operating modes, adjust or fine tune the configuration data, etc.

Various modifications can be made to the device 20 illustrated in FIG. 1. For example, a user interface or input/output devices can be incorporated into the first unit 22 or the second unit 24. In another example, the second unit 24 can include one or more microphones. Generally, the device 20 may include additional or fewer components arranged in any suitable manner. In some examples, the device 20 may include other components to process external audio signals, such as components that measure vibrations in the skull caused by audio signals and/or components that measure electrical outputs of portions of a person's hearing system in response to audio signals.

Figure 2:
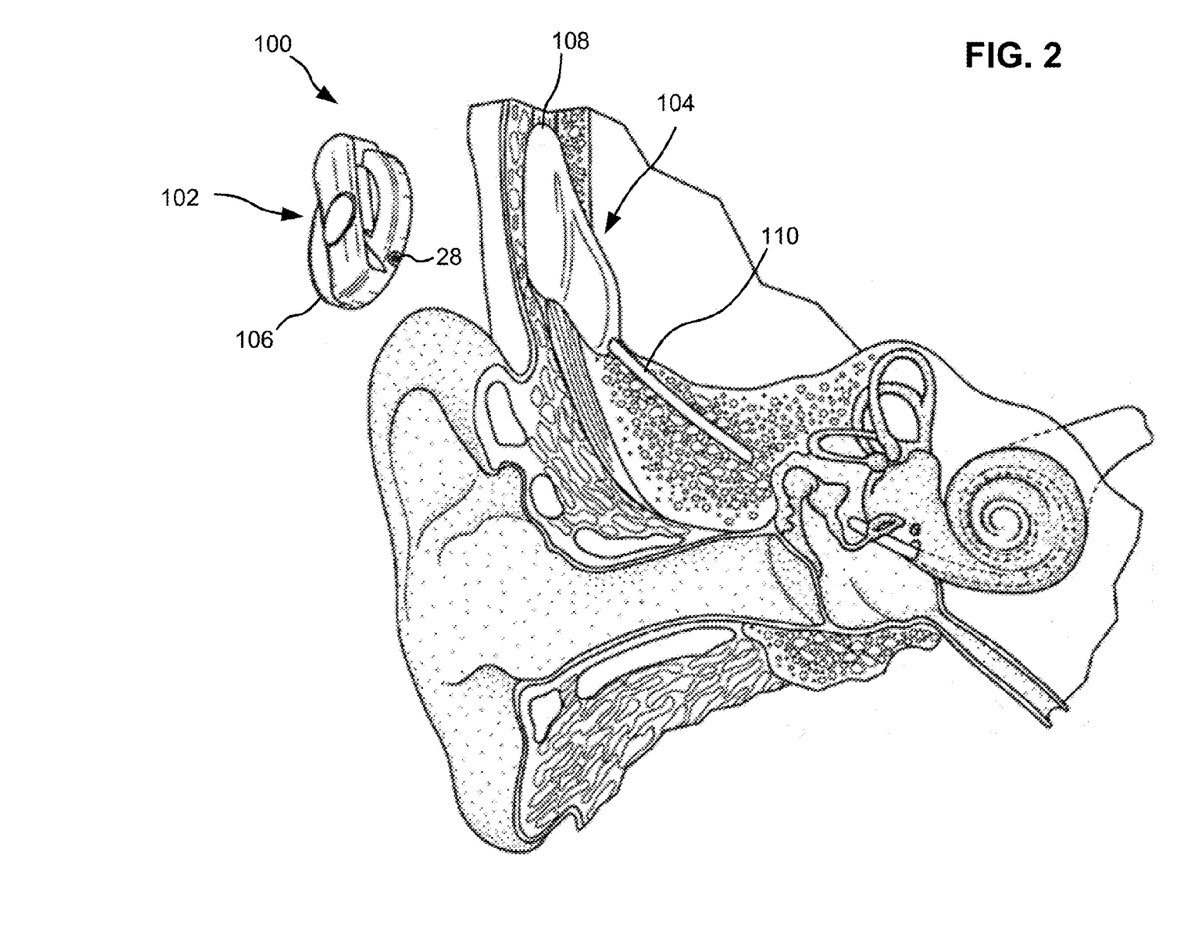
FIG. 2 is a partially cut-away, isometric view of a hearing prosthesis coupled to a recipient in accordance with an embodiment of the present disclosure.

Referring now to FIG. 2, an example hearing prosthesis 100 is shown coupled to a recipient's hearing system. The prosthesis 100 includes an external unit 102 that is directly or indirectly attached to the body of the recipient and an internal unit 104 that is temporarily or permanently implanted in the recipient. With reference to FIG. 1, the external unit 102 can correspond to the first unit 22, and the internal unit 104 can correspond to the second unit 24.

The external unit 102 includes a housing 106, within which are disposed various components. In FIG. 2, the external unit 102 and the housing are generally button-shaped. In one example, the external unit 102 includes sound processing components and external radio electronics. In this example, the external radio electronics includes an external coil along with associated circuitry to energize the coil and generate an alternating magnetic field. The sound processing unit can include a digital signal processor (DSP), a power source, and a magnetic transducer 28. As described above, the transducer 28 is configured to detect sound and to generate an audio signal representative of the detected sound. In one example, the transducer 28 includes a microphone. In other examples, the transducer 28 includes more than one microphone, one or more telecoil induction pickup coils, or other devices now known or later developed that are configured to detect sound and to generate electrical signals representative of the detected sound. In some embodiments, the transducer 28 may not be integrated into the sound processing unit, but rather can be a separate component of the external unit 102. The external unit 102 can also include a permanent magnet that is used to aid in the positioning of the external unit 102 with respect to the internal unit 104.

In other examples, the transducer can be a Hall effect transducer or sensor, a magnetic pressure transducer, a magnetic switch transducer or Reed sensor, a giant magneto resistance ("GMR") transducer, etc.

The internal unit 104 includes a housing 108 that hermetically seals various components. In one example, the internal unit 104 includes internal radio electronics and stimulation electronics. In the present example, the stimulation electronics include an electrode assembly 110, and the internal radio electronics include an internal coil and associated circuitry for processing signals induced in the internal coil by the alternating magnetic field. Further, the internal unit 104 can also include a permanent magnet that is used to aid in the positioning of the external unit 102 with respect to the internal unit.

The external and internal coils can be wire antenna coils comprised of multiple turns of electrically insulated single-strand or multi-strand wire, such as platinum or gold wire. The external and internal coils can also be integrated as a conductive track on a printed circuit board. In the example of FIG. 2, the external coil can be held in place and aligned with the implanted internal coil via the magnets noted above.

Figure 3:
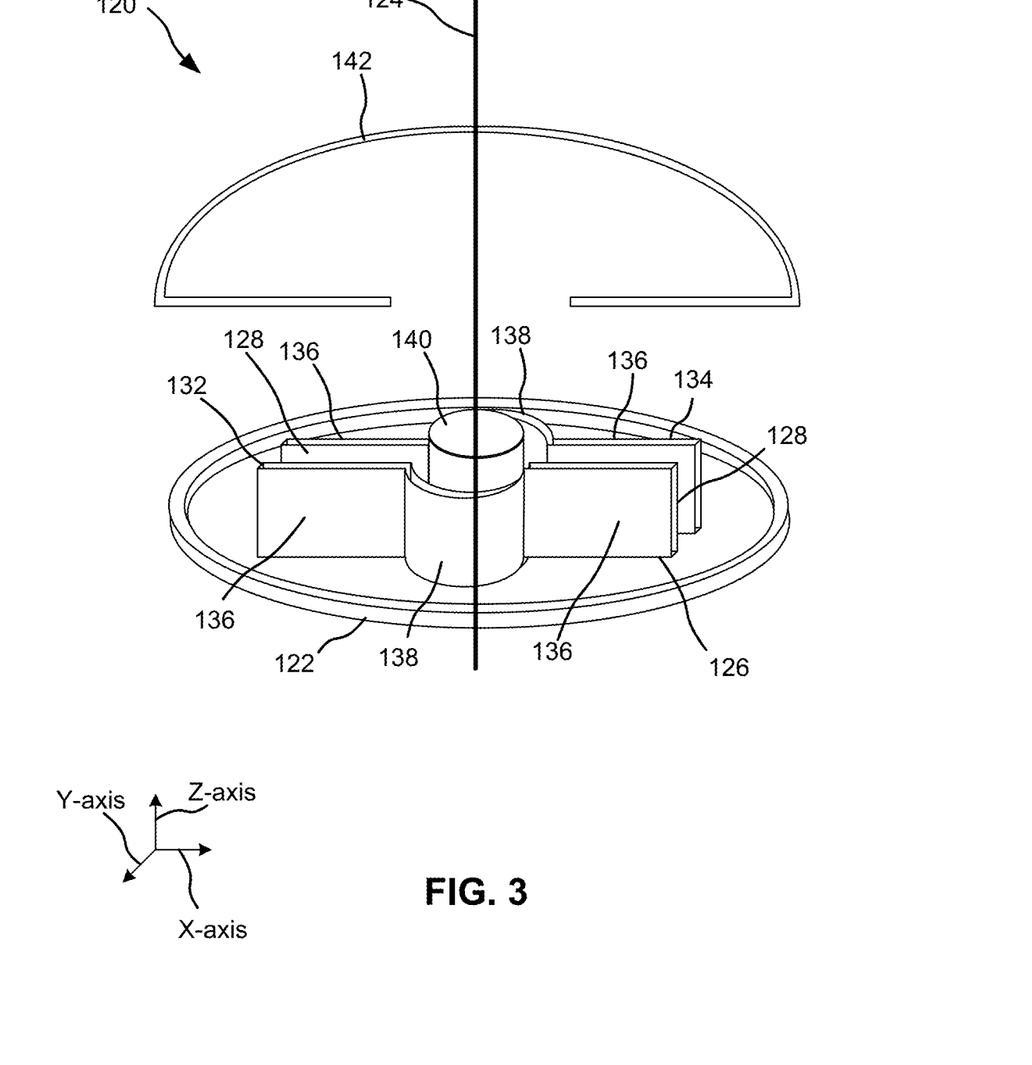
FIG. 3 is a diagrammatic, isometric view of an electronic device according to an embodiment of the present disclosure.

Referring now to FIG. 3, an example embodiment is illustrated of any one of the units 22, 24 of FIG. 1 or the units 102, 104 of FIG. 2. More particularly, FIG. 3 illustrates a unit 120 that includes radio electronics, which in the present example includes a coil 122. The coil 122 is disposed substantially in a first plane. The coil 122 can be any suitable shape, such as circular, ovular, rectangular, or any other geometric or abstract shape. For reference purposes, a 3-dimensional coordinate system is defined with an X-axis that is orthogonal to a Y-axis and to a Z-axis. Likewise, the Y-axis is orthogonal to the Z-axis. In FIG. 3, the coil 122 is disposed substantially in the XY-plane and the coil further defines a center axis that is substantially parallel to the Z axis. When an electrical signal is passed through the coil 122, the coil generates a magnetic field that is represented by a magnetic field line 124 along an axis of symmetry of the magnetic field. The magnetic field line 124 at the axis of symmetry is a straight line that is substantially parallel to the Z-axis.

The unit 120 further includes a substrate 126 that is substantially orthogonal to the coil 122 and to the XY-plane. As seen in FIG. 3, the substrate 126 extends substantially along the Z-axis and is disposed within an inner boundary of the coil 122. Further, in the present example, the substrate 126 includes a conductive ground surface or ground plane 128. Generally, the ground plane 128 is an electrically conductive surface that can be connected to an electrical ground point. For example, in a printed circuit board (PCB) substrate, the ground plane can be a continuous layer of copper foil glued on the substrate connected to the electrical ground point, which can be one terminal of a power supply.

In the present disclosure, one or more electrical components are coupled to the substrate 126 and to the ground plane 128. The substrate 126 and the ground plane 128 are disposed substantially orthogonal to the plane of the coil 122 and are also generally parallel to the magnetic field generated by the coil. This configuration helps to reduce noise and interference by decreasing a magnetic flux of the magnetic field that passes through the one or more components, the substrate, and the ground plane. The ground plane also helps to reduce noise and interference by providing a path for current pulses (such as eddy currents) to flow to the ground point, instead of flowing to other electrical components. By reducing noise and interference, this configuration improves signal quality in the unit 120 and over the RF link between the coil 122 and other radio electronics. Further, this configuration also helps to improve the power efficiency of the unit 120 and of the RF link between the coil 122 and other radio electronics.

In the example of FIG. 3, the substrate 126 includes a first portion 132 that is spaced from a second portion 134. Each of the first and second portions 132, 134 includes generally planer end sections 136 and a curved middle section 138 disposed between the end sections. The curved middle section 138 is generally disposed around a permanent magnet 140, which has a cylindrical shape and is positioned at about the center axis of the coil 122 with a base of the magnet substantially parallel to the XY-plane. The magnet 140 has a N-S axis (or axis of symmetry) that is substantially parallel to the Z-axis. The magnet 140 can be used to help position the unit 120 with respect to another unit so that the coil 122 is aligned with radio electronics of the other unit.

Further, the unit 120 of FIG. 3 illustrates a housing 142 that is configured to be disposed over the substrate 126. Generally, the unit 120, which can be a hearing prosthesis or other medical or non-medical device, is designed to have a relatively small size so that it is unobtrusive when in use. In one example, the unit 120 has a diameter that is less than about 10 cm and a height that is less than about 3 cm. For example, the unit 120 can have a diameter that is about 5 cm and a height that is about 10 mm.

Figure 4:
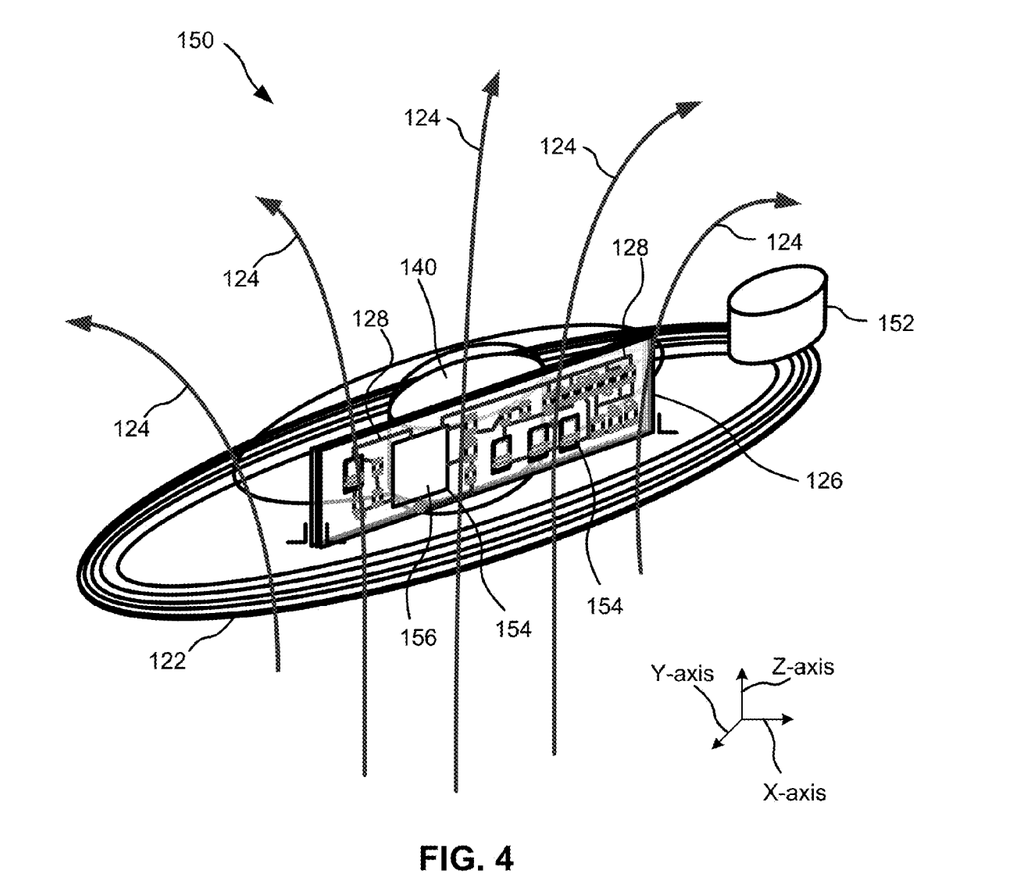
FIG. 4 is a diagrammatic, isometric view of an electronic device according to an embodiment of the present disclosure.

FIG. 4 illustrates another example unit 150 that, similarly to the unit 120 of FIG. 3, includes a coil 122 substantially disposed in the XY-plane, a substrate 126 that is substantially orthogonal to the coil and to the XY-plane, ground planes 128 included on the substrate, and a magnet 140. The unit 150 further includes a power source 152 and a plurality of electrical components 154 coupled to the substrate 126 and to the ground plane 128.

In FIG. 4, the magnetic field generated by the coil 122 is represented by a plurality of magnetic field lines 124. The magnetic field lines 124 are shown radially spaced from the axis of symmetry of the magnetic field. More particularly, the field lines 124 are shown curved, with field lines that are radially spaced farther from the axis of symmetry being curved to a greater degree than field lines that are radially spaced closer to the axis of symmetry. Although the magnetic field lines 124 are curved, the substrate 126 and the ground planes 128 remain substantially parallel to the field lines, which reduces the magnetic flux that passes through the components 154, the substrate, and the ground plane.

The components 154 can include any hearing prosthesis components. For example, the components can include sensors, such as a microphone or Hall sensor. In FIG. 4, a sensor area 156 of the sensor is configured to receive an audio signal (e.g., in the case of a microphone) or is configured to detect a magnetic field from a permanent magnet that is external to the unit 150 (e.g., in the case of a Hall sensor). The sensor area 156 can also be arranged substantially orthogonally to the coil 122 and/or substantially parallel to the magnetic field lines 124. This arrangement of the sensor area 156 reduces adverse effects that the magnetic field lines 124 may have on the microphone.

In the case of the Hall sensor, this arrangement also causes the Hall sensor to not be substantially affected by a magnetic field of a permanent magnet that can be included in the unit 150 (e.g., the magnet 140 with an axis of symmetry that is substantially orthogonal to the XY-plane). As discussed herein, permanent magnets can be used to position the unit 150 with respect to another unit. The Hall sensor can also be used to detect the presence of a second permanent magnet that is included in the other unit. The detection of the second permanent magnet can be used as a switch to cause the coil 122 to generate the magnetic field to communicate power and/or data to the other unit.

Figure 5:
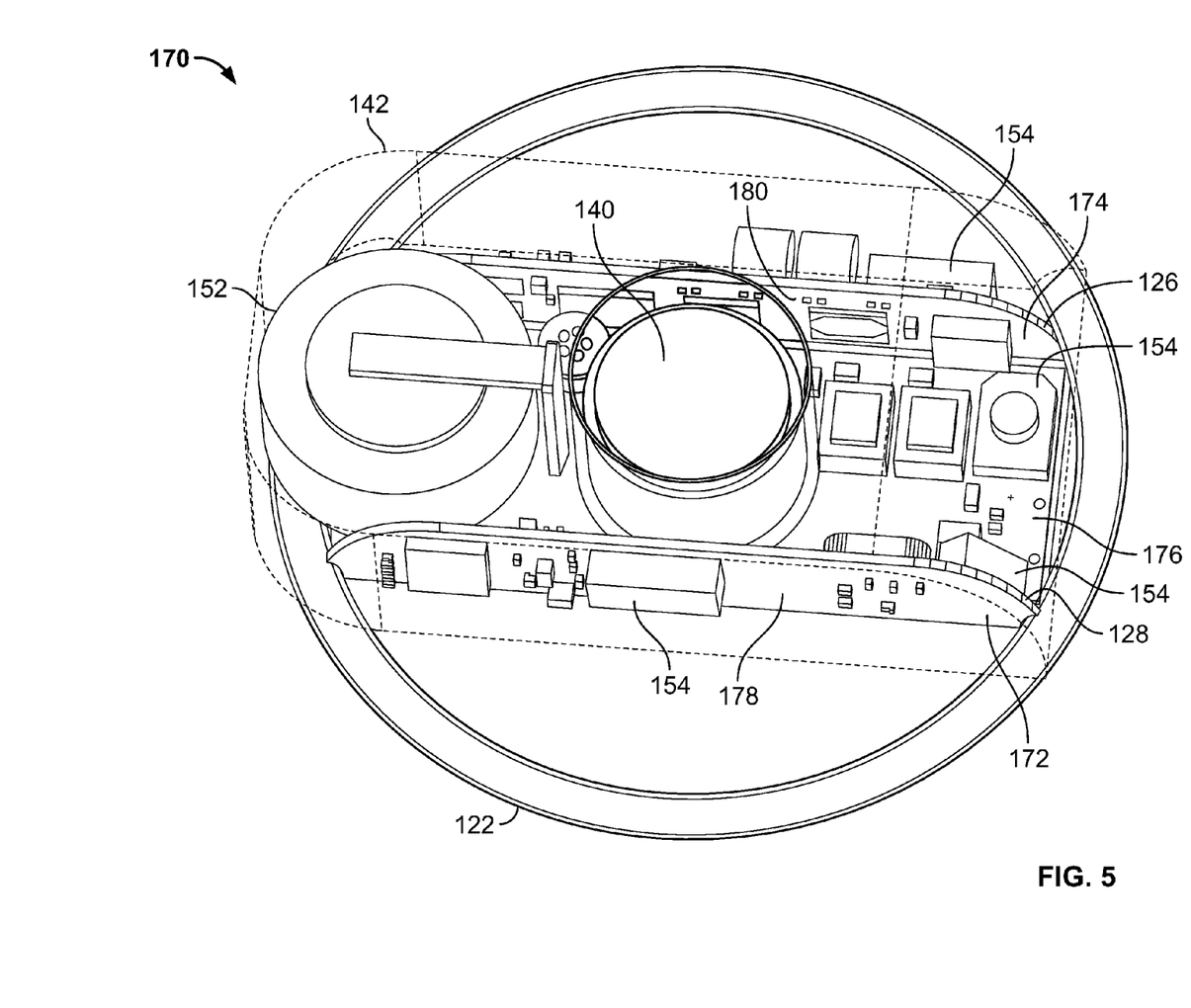
FIG. 5 is an isometric view of an electronic device according to an embodiment of the present disclosure.

FIG. 5 illustrates another example unit 170 that includes a coil 122 that is disposed in a generally horizontal plane, a substrate 126, a ground plane 128, a magnet 140, a power source 152, a plurality of electrical components 154, and a housing 142. In the example of FIG. 5, the substrate 126 includes a first side portion 172 that is substantially orthogonal to the coil 122 and a second side portion 174 that is spaced from and parallel to the first side portion. The first and second side portions 172, 174 are generally disposed in a vertical plane. The substrate also includes a bottom portion 176 that is disposed between the first and second side portions and is generally in the same horizontal plane as the coil. Consequently, the substrate 126 has a generally U-shaped cross section.

In the present example, the first side portion 172, the second side portion 174, and the bottom portion 176 can be at least partially coupled together or can be completely separate portions. Further, in the present example, the ground plane 128 can be included in only the first side portion 172 and/or the second side portion 174, and not in the bottom portion 176. Still further, the unit 170 includes certain components 154 that are coupled to the first and second side portions 172, 174 and to the ground plane 128, and other components that are coupled to the bottom portion 176 and not to the ground plane. In another example, the bottom portion 176 also includes the ground plane 128 that is substantially smaller than the first and/or second electrical ground planes of the first and/or second side portions 172, 174. Illustratively, the ground plane included in the bottom portion 176 can have a conductive surface area that is about 25% or less than a conductive surface area of the first and/or second side portions 172.

The components 154 coupled to the side portions 172, 174 include components that are sensitive to noise and interference from a varying magnetic field. Such components include transducers and microprocessors, for example. The components 154 coupled to the bottom portion 176 can include components that are less sensitive to noise and interference from the varying magnetic field. These less sensitive components can include push buttons and a power source, for example.

In addition, the substrate 126 shown in FIG. 5 includes a first side 178 and an opposing second side 180. In FIG. 5, the components 154 are coupled to the first and second sides 178, 180 of the substrate 126, such that a greater number of components can be coupled to the substrate compared to coupling components only to a single side of the substrate.

Figure 6:
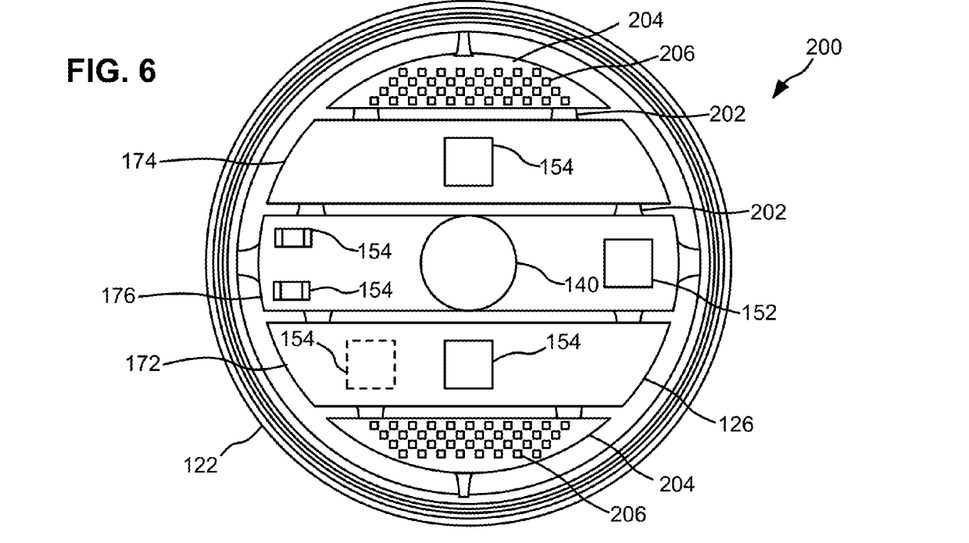
FIG. 6 is a diagrammatic, plan view of an electronic device according to an embodiment of the present disclosure.
Figure 7:
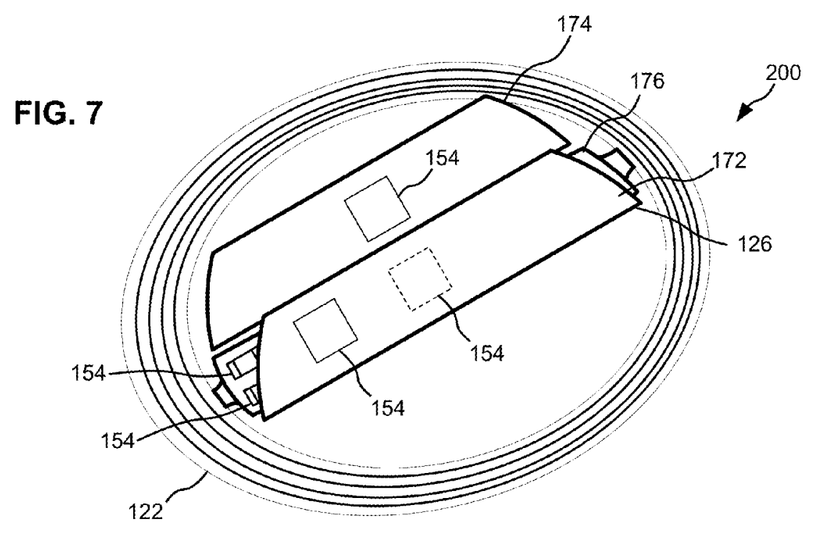
FIG. 7 is an isometric view of the electronic device of FIG. 6.

Referring now to FIGS. 6 and 7, another example unit 200 is disclosed that is similar to the unit 170 of FIG. 5. More particularly, the unit 200 includes a coil 122, a substrate 126 that includes a ground plane (not shown), a magnet 140, a power source 152, and a plurality of electrical components 154. Further, the substrate 126 of the unit 200 also includes a first side portion 172, a second side portion 174, and a bottom portion 176. As described above in relation to FIG. 5, the ground plane can be removed from the bottom portion 176, or the bottom portion may include the ground plane and the components 154 may not be coupled to the ground plane of the bottom portion.

In FIG. 6, the first and second side portions 172, 174 are disposed in the same plane as the bottom portion 176. In FIG. 7, the first and second side portions 172, 174 are folded to be disposed orthogonally to the bottom portion 176. The side portions 172, 174 and the bottom portion 176 can be connected by flexible joints 202 to facilitate folding the side portions from the configuration shown in FIG. 6 to the configuration shown in FIG. 7.

Generally, the configuration in FIG. 6 can represent the unit 200 during or just after a production or manufacturing stage, and the configuration in FIG. 7 can represent the unit configured for normal use. In the configuration of FIG. 6, the substrate 126 also includes test portions 204 and test points 206 disposed on the test portions. The test points 206 can be used to verify the operation of various functions of the unit 200 before the unit is configured for normal everyday use. Consequently, FIG. 7 shows the unit 200 with the test portions 204 removed.

Figure 8:
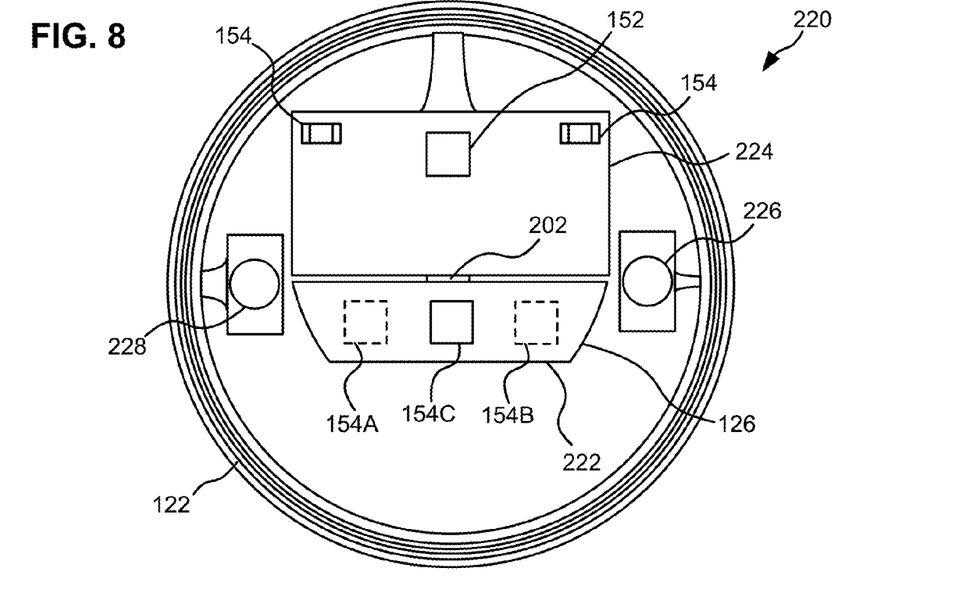
FIG. 8 is a diagrammatic, plan view of an electronic device according to an embodiment of the present disclosure.
Figure 9:
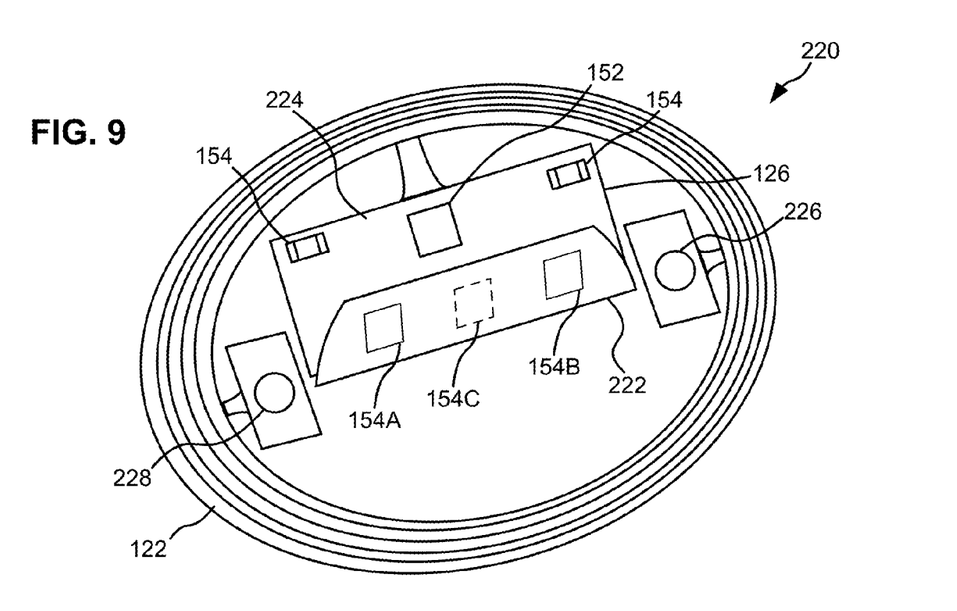
FIG. 9 is an isometric view of the electronic device of FIG. 8.

FIGS. 8 and 9 illustrate another example unit 220 that also includes a coil 122, a substrate 126 that includes a ground plane (not shown), a power source 152, and a plurality of electrical components 154. Further, the substrate 126 in FIG. 8 includes a first portion 222 and a second portion 224. In the present example, the ground plane can be removed from the second portion 224, or the second portion may include the ground plane and the components 154 may not be coupled to the ground plane of the second portion.

In FIG. 8, the first and second portions 222, 224 are disposed in the same plane as the coil 122. In FIG. 9, the first portion 222 is folded to be disposed orthogonally to the second portion 224 and to the coil 122. The first portion 222 is connected by a flexible joint 202 to the second portion 224 to facilitate folding the first portion from the configuration shown in FIG. 8 to the configuration shown in FIG. 9.

Further, in FIG. 9, the first portion 222 includes a first microphone 154A, a second microphone 154B, and a processor 154C. Each of the microphones and the processor is coupled to the substrate 126 and to the ground plane. This configuration of the microphones and the processor can provide a directional microphone function that is resistant to noise and interference from the varying magnetic field generated by the coil, because these components and the planes or circuit traces coupled there between are disposed on the same substrate portion that is generally parallel to the varying magnetic field.

In FIGS. 8 and 9, the unit 220 also includes a first magnet 226 and a second magnet 228. The first magnet 226 is spaced from the second magnet 228. The first and second magnets 226, 228 are also disposed generally symmetrically with respect to a center axis of the coil 122. This arrangement allows the first and second magnets to be used to align the unit 220 with another unit or device that may include its own corresponding first and second magnets. Further, this arrangement allows the magnets to be spaced away from the axis of symmetry of the magnetic field generated by the coil 122 so that the first portion 222 can intersect the axis of symmetry, which also corresponds to the center axis of the coil. Consequently, the first portion 222 can couple electrical components closer to the axis of symmetry where the magnetic field lines are generally straight.

Figure 10:
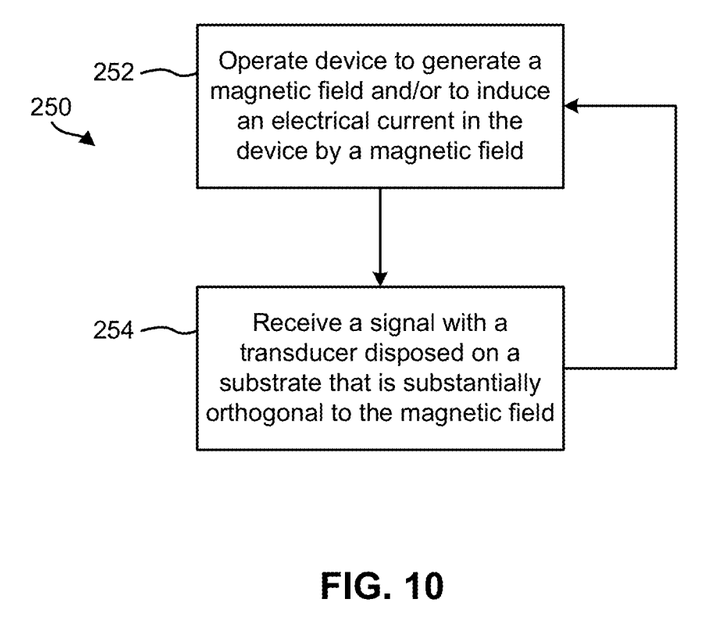
FIG. 10 is a flowchart showing a method for operating an electronic device.

Referring now to FIG. 10 and with further reference the description above, one example method 250 is illustrated for operating a device in an alternating magnetic field. The method 250 of FIG. 10 can be implemented by one or more of the devices or units described above. In the method 250, at block 252, a device passes a first electrical signal through a coil or some other radio electronics of the device. The electrical signal causes the coil to generate a first magnetic field that represents the first electrical signal. In one example, each of the first electrical signal and the first magnetic field includes at least one of power or audio data. The first magnetic field communicates power and/or data to a second unit, which, in one example, can be a hearing prosthesis unit that is implanted in a recipient. Accordingly, the device can be an external medical device that is configured to communicate with the implantable medical device unit through the varying magnetic field.

Alternatively or in conjunction, at block 252, a second magnetic field induces a second electrical signal in the coil. In this example, the second electrical signal represents the second magnetic field, and each of the second electrical signal and the second magnetic field includes at least one of power or audio data. The second magnetic field can be generated by another unit of a hearing prosthesis to communicate power and/or data to the device. The other unit of the hearing prosthesis can be an implantable unit or an external unit.

At block 254, the device receives a signal through a transducer, such as a microphone and/or a Hall sensor. The transducer is coupled to a substrate, and the substrate is substantially orthogonal to a plane of the coil and the substrate is also substantially parallel to one or more of the first and second magnetic fields. The substrate can also include a ground plane coupled to the transducer, as discussed above. In one example, the received signal is an audio signal, and the device can use the received audio signal to generate the first electrical signal that is passed through the coil, as described in relation to block 252.

Alternatively or in addition, the received signal can be a signal received by a Hall sensor. The received signal can be indicative of the device being in proximity or alignment with another unit. This signal from the Hall sensor can then be used to responsively trigger the functions of block 252 to be performed.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. An external device of an implantable medical system comprising:
    a coil substantially disposed in an XY-plane, wherein when a first AC electrical signal is passed through the coil, the coil generates an alternating magnetic field that represents the AC electrical signal, wherein the electrical signal includes at least one of power or data;
    a cylindrical shaped permanent magnet with base substantially parallel to the XY-plane, wherein the magnet is used to position the external device with respect to an implantable device;
    a printed circuit board that includes at least a portion that is substantially orthogonal to the XY-plane, wherein the portion includes an electrical ground plane; and
    at least one sensor coupled to the portion of the substrate and to the ground plane.

2. The external device of claim 1, wherein the at least one sensor includes a magnetic transducer.

3. The external device of claim 1, wherein the at least one sensor includes a Hall sensor for sensing a second magnetic field generated by a permanent magnet included in the implantable device, wherein, responsive to sensing the second magnetic field, the coil is configured to generate the first magnetic field to communicate the at least one of power or data to the implantable device.

4. The external device of claim 1, wherein the at least one sensor includes at least one acoustic transducer, wherein the transducer receives an audio signal and converts the audio signal into the data included in the electrical signal.

5. The external device of claim 1, wherein the substrate further includes a second portion that is substantially parallel to the XY-plane.

6. The external device of claim 5, wherein the substrate includes a third portion that is orthogonal to the XY-plane and is spaced from the first portion, wherein the third portion includes an electrical ground plane, and wherein the third portion is configured to couple a second electrical component to the third portion.

7. The external device of claim 6, wherein the electrical ground plane of the first portion is electrically connected to the electrical ground plane of the third portion via a third electrical ground plane included in the second portion, wherein the third electrical ground plane is substantially smaller in conductive surface area than the first and second electrical ground planes of the first and third portions.

8. The device of claim 1, wherein the portion of the substrate includes a first side and an opposing second side, wherein the at least one sensor is disposed on the first side and coupled to the ground plane, and an electrical component is disposed on the second side and coupled to the ground plane.

9. The device of claim 1, wherein the sensor includes a sensor area that is configured to receive an audio signal or to detect a magnetic field from a permanent magnet, and wherein the sensor area is disposed substantially orthogonal to the XY-plane.

10. An external medical device comprising:
    radio electronics configured to generate an alternating magnetic field, wherein the alternating magnetic field transmits data from the external medical device to an implantable medical device that is configured to be implanted in a recipient;
    a circuit substrate positioned substantially parallel to the direction of the alternating magnetic field lines, wherein the circuit substrate includes an electrical ground plane, and wherein the circuit substrate is configured to couple an electrical component to the ground plane.

11. The external medical device of claim 10, further comprising the electrical component coupled to the ground plane, wherein the electrical component includes a transducer, wherein the radio electronics is configured to receive a signal from the transducer, and wherein the radio electronics is configured to use the received signal to generate the alternating magnetic field.

12. The external device of claim 11, wherein the circuit substrate includes a first side and an opposing second side, wherein the transducer is coupled to the first side of the circuit substrate, and wherein a second electrical component is coupled to the second side of the circuit substrate and to the ground plane.

13. The external device of claim 10, further comprising a second circuit substrate and a third circuit substrate, wherein the second circuit substrate is substantially orthogonal to the first circuit substrate, wherein the third circuit substrate is positioned substantially parallel to the magnetic field and is spaced from the first circuit substrate, wherein the third circuit substrate includes a second electrical ground plane, and further comprising a second electrical component coupled to the third circuit substrate and to the second electrical ground plane.

14. The external device of claim 10, wherein the alternating magnetic field defines an axis of symmetry, the device further comprising a magnet that is disposed substantially along the axis of symmetry.

15. The external device of claim 10, wherein the alternating magnetic field defines an axis of symmetry, the device further comprising a first magnet and a second magnet, wherein the first magnet and the second magnet are spaced from one another and are disposed substantially symmetrically with respect to the axis of symmetry.

16. A method comprising:
operating a first device that includes a coil that is substantially disposed in an XY-plane, wherein when an AC electrical signal is passed through the coil, the coil generates an alternating magnetic field that represents the electrical signal, wherein the electrical signal includes at least one of power or data, wherein the magnetic field communicates a representation of the at least one of power or data to a second device implanted in a recipient; and receiving a signal with a sensor, wherein the sensor is coupled to an electrical ground plane of the device, and wherein the electrical ground plane is substantially orthogonal to the XY-plane.

17. The method of claim 16, wherein the sensor includes at least one magnetic transducer.

18. The method of claim 16, wherein the sensor includes at least one acoustic transducer, wherein the transducer receives an audio signal and converts the audio signal into the data included in the AC electrical signal.

19. The method of claim 16, wherein the first device is a unit of a hearing prosthesis.

20. The method of claim 19, wherein the first device is a button-shaped device.

* * * * *